(12) United States Patent
Kuisell et al.

(10) Patent No.: US 7,827,848 B2
(45) Date of Patent: Nov. 9, 2010

(54) OXYGEN SENSOR AND METHOD FOR MANUFACTURING THE OXYGEN SENSOR

(75) Inventors: Richard C. Kuisell, Lapeer, MI (US); Michel Carlé, Luxembourg (LU)

(73) Assignee: Delphi Technologies, Inc., Troy, MI (US)

( * ) Notice: Subject to any disclaimer, the term of this patent is extended or adjusted under 35 U.S.C. 154(b) by 605 days.

(21) Appl. No.: 11/839,340

(22) Filed: Aug. 15, 2007

(65) Prior Publication Data
US 2009/0044598 A1  Feb. 19, 2009

(51) Int. Cl.
*G01N 7/00* (2006.01)
(52) U.S. Cl. .................................... 73/23.31
(58) Field of Classification Search ........... None
See application file for complete search history.

(56) References Cited
U.S. PATENT DOCUMENTS 6,153,071 A  11/2000 Omara et al.
6,344,134 B1 * 2/2002 Yamada et al. ............. 205/781
6,579,435 B2 * 6/2003 Wang et al. ................ 204/425
6,773,565 B2 * 8/2004 Kunimoto et al. .......... 204/425

OTHER PUBLICATIONS

International Search Report dated Nov. 5, 2008.

* cited by examiner

*Primary Examiner*—Hezron Williams
*Assistant Examiner*—Mark Shabman
(74) *Attorney, Agent, or Firm*—Thomas N. Twomey

(57) ABSTRACT

An oxygen sensor and a method for manufacturing the oxygen sensor are provided. The oxygen sensor includes a zirconia layer having first and second sides. The second side is opposite the first side. The oxygen sensor further includes a first electrode disposed on the first side of the zirconia layer. The oxygen sensor further includes a second electrode disposed on the second side of the zirconia layer. The oxygen sensor further includes a porous channel structure configured to route air therethrough to the first electrode while preventing hydrocarbons from flowing therethrough and contacting the first electrode, such that a signal between the first and second electrodes is indicative of an amount of oxygen in exhaust gases contacting the second electrode.

15 Claims, 2 Drawing Sheets

US 7,827,848 B2

OXYGEN SENSOR AND METHOD FOR MANUFACTURING THE OXYGEN SENSOR

BACKGROUND

An oxygen sensor has been utilized to measure oxygen in exhaust streams. The oxygen sensor has an open channel that allows ambient air to fluidly communicate with a reference electrode. A problem associated with the oxygen sensor recognized by the inventors herein, however, is that the open channel can undesirably allow hydrocarbons to fluidly communicate with the reference electrode that may cause the oxygen sensor to generate a signal that does not accurately indicate an oxygen concentration in exhaust gases communicating with a sensing electrode of the oxygen sensor.

The inventors herein have recognized a need for an improved oxygen sensor that minimizes and/or eliminates the foregoing problem.

SUMMARY

An oxygen sensor in accordance with an exemplary embodiment is provided. The oxygen sensor includes a zirconia layer having first and second sides. The second side is opposite the first side. The oxygen sensor further includes a first electrode disposed on the first side of the zirconia layer. The oxygen sensor further includes a second electrode disposed on the second side of the zirconia layer. The oxygen sensor further includes a porous channel structure configured to route air therethrough to the first electrode while preventing hydrocarbons from flowing therethrough and contacting the first electrode, such that a signal between the first and second electrodes is indicative of an amount of oxygen in exhaust gases contacting the second electrode.

A method for manufacturing an oxygen sensor in accordance with another exemplary embodiment is provided. The method includes disposing a first electrode on a first side of a zirconia layer. The method further includes disposing a second electrode on a second side of the zirconia layer. The second side is opposite the first side. The method further includes disposing a carbon-ceramic mixture on a first layer. The method further includes disposing the first layer adjacent the zirconia layer such that the carbon-ceramic mixture is disposed adjacent the first electrode. The method further includes firing the zirconia layer, the first and second electrodes, the carbon-ceramic mixture, and the first layer to form the oxygen sensor such that the carbon-ceramic mixture transitions to a porous channel structure. The porous channel structure is configured to route air therethrough to the first electrode while preventing hydrocarbons from flowing therethrough and contacting the first electrode.

A system for determining an amount of oxygen in exhaust gases in accordance with another exemplary embodiment is provided. The system includes an oxygen sensor having a zirconia layer, first and second electrodes and a porous channel structure. The zirconia layer has first and second sides. The second side is opposite the first side. The first electrode is disposed on the first side of the zirconia layer. The second electrode is disposed on the second side of the zirconia layer. The porous channel structure is configured to route air therethrough to the first electrode while preventing hydrocarbons from flowing therethrough and contacting the first electrode, such that a signal between the first and second electrodes is indicative of the amount of oxygen in exhaust gases contacting the second electrode. The system further includes a microprocessor configured to receive the signal from the oxygen sensor. The microprocessor is further configured to determine an oxygen value corresponding to the amount of oxygen in the exhaust gases based on the signal. The microprocessor is further configured to store the oxygen value in a memory device.

DETAILED DESCRIPTION OF EXEMPLARY EMBODIMENTS

Figure 1:
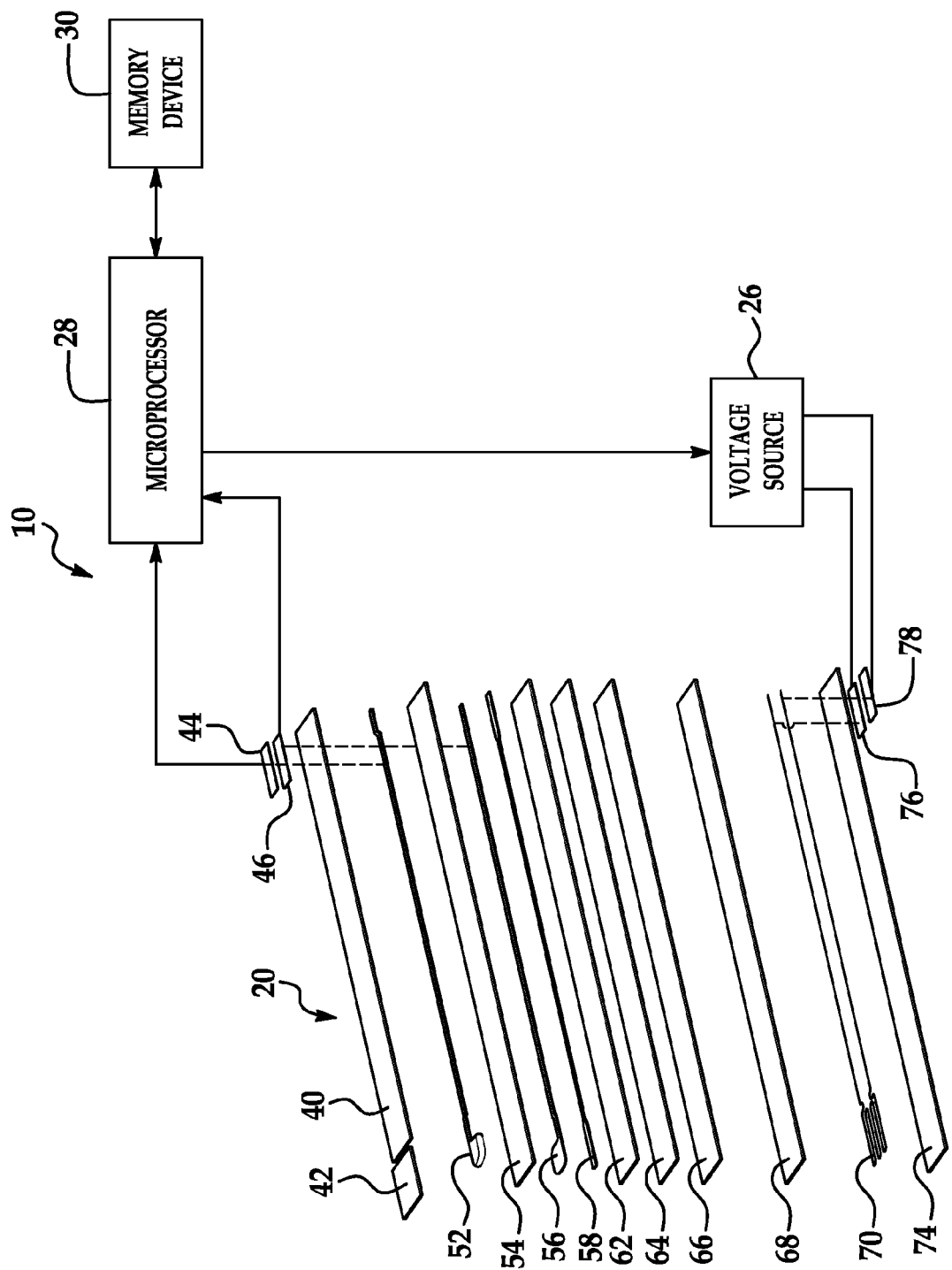
FIG. 1 is a schematic of an oxygen monitoring system having an exploded view of an oxygen sensor in accordance with an exemplary embodiment.
Figure 2:
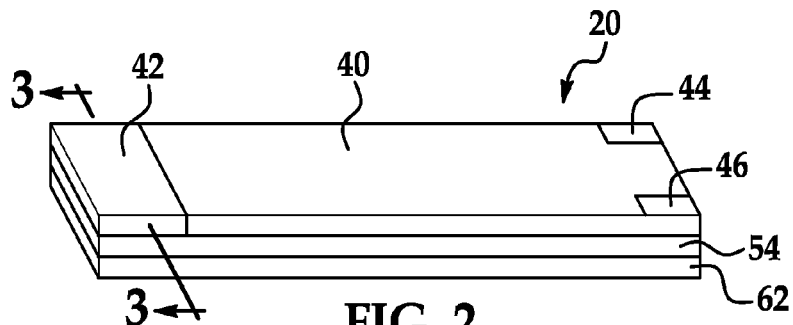
FIG. 2 is a schematic of a sensing structure of the oxygen sensor of FIG. 1.
Figure 3:
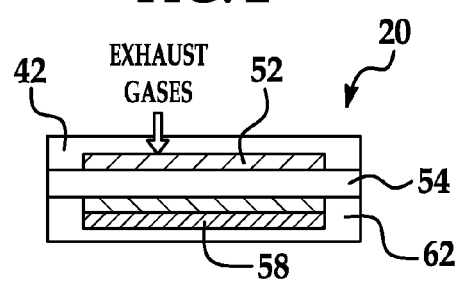
FIG. 3 is a cross-sectional schematic of the sensing structure of the oxygen sensor of FIG. 2 along lines 3-3.

Referring to FIGS. 1-3, an oxygen monitoring system 10 for determining a concentration of oxygen in exhaust gases in accordance with an exemplary embodiment is illustrated. The oxygen monitoring system 10 includes an oxygen sensor 20, a voltage source 26, a microprocessor 28, and a memory device 30.

The oxygen sensor 20 is provided to generate a signal that is indicative of an oxygen concentration level in exhaust gases communicating with the oxygen sensor 20. The oxygen sensor 20 includes a ceramic layer 40, a porous ceramic protective cover 42, contact pads 44, 46, an electrode 52, a zirconia layer 54, an electrode 56, a porous channel structure 58, ceramic layers 62, 64, 66, 68, a heater coil 70, a ceramic layer 74, and contact pads 76, 78.

The electrode 56 is disposed on a first side of the zirconia layer 54. The electrode 52 is disposed on the second side of the zirconia layer 54 opposite the first side. The porous ceramic protective cover 42 is disposed on the zirconia layer 54 such that a portion of the electrode 52 is disposed between the porous ceramic protective cover 42 and the zirconia layer 54. Exhaust gases communicating with the porous ceramic protective cover 42 migrate through the porous ceramic protective cover 42 to fluidly communicate with the electrode 52. The ceramic layer 40 is disposed on the zirconia layer 54 such that another portion of the electrode 52 is disposed between the ceramic layer 40 and the zirconia layer 54.

The contact pads 44, 46 are disposed on the ceramic layer 40 opposite the zirconia layer 54. The contact pads 44, 46 are electrically coupled to the electrodes 52, 56, respectively and are further electrically coupled to the microprocessor 28. During operation, a signal between the electrodes 52, 56 is indicative of a concentration of oxygen in exhaust gases communicating with the electrode 52. The signal can comprise a voltage between the electrodes 52, 56, or a pumping current flowing between the electrodes 52, 56.

The porous channel structure 58 is provided to route air to the electrode 56 which is also referred to as a reference electrode. The porous channel structure 58 is further configured to prevent hydrocarbons from flowing therethrough. In one exemplary embodiment, the porous channel structure 58 is constructed from a carbon-ceramic mixture that is deposited on the ceramic protective cover 42 and then fired at temperatures in a range of 20-1500 degrees Celsius to form the porous channel structure 58 on the ceramic layer 62.

During the firing process, the carbon in the carbon-ceramic mixture is burnt away leaving spaces in the mixture where the carbon was originally present to form the porous channel structure 58. In one exemplary embodiment, the porous channel structure 58 comprises a porous alumina structure. In another exemplary embodiment, the porous channel structure 58 comprises a porous zeolite channel structure. Another advantage of the porous channel structure 58 is that the structure 58 can have a substantially uniform cross-sectional size in desired regions.

The ceramic layer 62 is disposed on the zirconia layer 54 such that the electrode 56 is disposed between the ceramic layer 62 and the zirconia layer 54. The ceramic layer 64 is disposed on the ceramic layer 62 opposite the zirconia layer 54. The ceramic layer 66 is disposed on the ceramic layer 64 opposite the ceramic layer 62. The ceramic layer 68 is disposed on the ceramic layer 66 opposite the ceramic layer 64. The ceramic layers 62, 64, 66, 68 electrically insulate the sensing structure comprising the electrodes 52, 56 and zirconia layer 54, from the heating coil 70.

It should be noted that in one exemplary embodiment, at least a portion of the ceramic layers 40, 62, 64, 66, 68 and 74 are constructed from alumina. In another alternative embodiment, at least a portion of the layers 40, 62, 64, 66, 68 and 74 are constructed from zirconia. However, it should be noted that in other alternative embodiments, other ceramic materials known to those skilled in the art can be utilized to construct layers 40, 62, 64, 66, 68 and 74. Further, it is noted that the number of ceramic layers of oxygen sensor 20 can vary from those shown in FIG. 1.

The heating coil 70 is provided to generate heat for maintaining the oxygen sensor 20 within a predetermined temperature range. The heating coil 70 generates heat in response to a voltage received from the voltage source 26 via the contact pads 76, 78. The heating coil 70 is disposed between the ceramic protective cover 42 layers 68 and 74.

The contact pads 76, 78 are disposed on the ceramic protective cover 42 layer 74 opposite the ceramic protective cover 42 layer 68. The contact pads 76, 78 are electrically coupled to the heater coil 70 and to the voltage source 26.

The voltage source 26 is provided to generate a voltage for inducing the heater coil 70 to generate heat. In particular, the voltage source 26 generates the voltage in response to a control signal received from the microprocessor 28.

The microprocessor 28 is provided to receive a signal either directly or indirectly from the electrodes 52, 56 of the oxygen sensor 20 indicative of a concentration of oxygen in exhaust gases communicating with the electrode 52. The microprocessor 28 is further configured to determine an oxygen concentration value in response to the signal from the electrodes 52, 56 of the oxygen sensor 20. A oxygen sensor 28 is further configured to store the oxygen concentration value in the memory device 30. The microprocessor 28 is electrically coupled either directly or indirectly to the contact pads 44, 46, the voltage source 26, and the memory device 30.

Referring to FIG. 3, a brief explanation of how the electrodes 56, 52 receive air and exhaust gases, respectively, will now be explained. Air migrates from an end of the porous channel structure 58 through the porous channel structure 58 to fluidly communicate with the electrode 56. Further, exhaust gases migrate through the porous ceramic protective cover 42 to fluidly communicate with the electrode 52.

Figure 4:
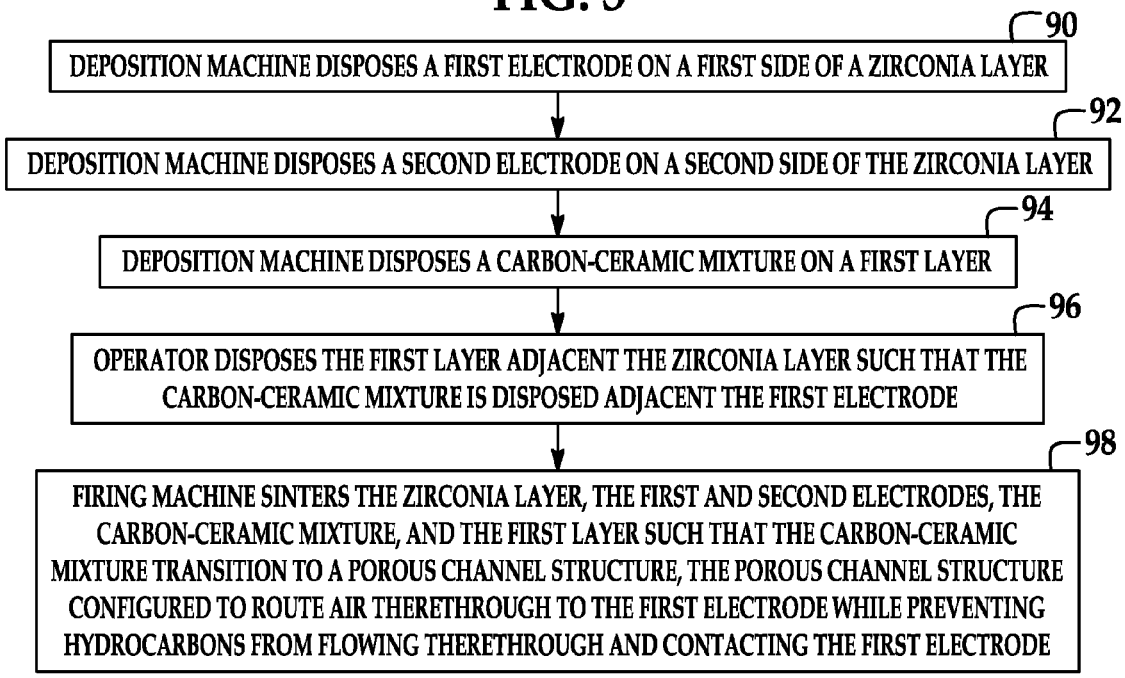
FIG. 4 is a flowchart of a method for manufacturing the oxygen sensor of FIG. 1 in accordance with another exemplary embodiment.
Figure 5:
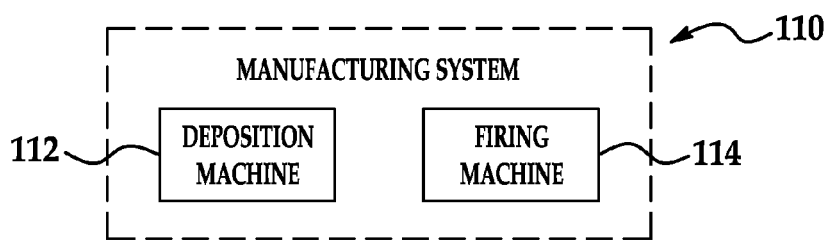
FIG. 5 is a schematic of a manufacturing system for manufacturing the oxygen sensor of FIG. 1.

Referring to FIG. 4, a flowchart of a method for manufacturing the oxygen sensor 20 will now be explained. It should be noted that the oxygen sensor 20 can be manufactured utilizing the manufacturing system 110 illustrated in FIG. 5.

At step 90, the deposition machine 112 disposes the electrode 56 on a first side of the zirconia layer 54.

At step 92, the deposition machine 112 disposes the electrode 52 on a second side of the zirconia layer 54.

At step 94, the deposition machine 112 disposes a carbon-ceramic mixture on the layer 62.

At step 96, an operator disposes the layer 62 adjacent the zirconia layer 54 such that the carbon-ceramic mixture is disposed adjacent the electrode 56.

At step 98, the firing machine 114 fires the zirconia layer 54, the electrodes 56, 52, the carbon-ceramic mixture, and the layer 62 such that the carbon-ceramic mixture transitions to the porous channel structure 58. The porous channel structure 58 is configured to route air therethrough to the electrode 56 while preventing hydrocarbons from flowing therethrough and contacting the electrode 56. In one exemplary embodiment, the firing machine 114 comprises a kiln that heats the layers of the oxygen sensor 20 to a temperature in a range of 20-1500 degrees Celsius.

The oxygen sensor and method for manufacturing the oxygen sensor represent a substantial advantage over other sensors and methods. In particular, the oxygen sensor and method provide a technical effect of utilizing a porous channel structure that routes air to a reference electrode while preventing hydrocarbons from flowing therethrough and contacting the reference electrode. As result, the oxygen sensor can generate a signal that more accurately indicates a concentration of oxygen in exhaust gases, as compared to other sensors.

While the invention has been described with reference to exemplary embodiments, it will be understood by those skilled in the art that various changes may be made and equivalent elements may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed for carrying this invention, but that the invention will include all embodiments falling within the scope of the appended claims. Moreover, the use of the terms, first, second, etc. are used to distinguish one element from another. Furthermore, the use of the terms a, an, etc. do not denote a limitation of quantity, but rather denote the presence of at least one of the referenced items.

What is claimed is:

1. An oxygen sensor, comprising:
a zirconia layer having first and second sides, the second side being opposite the first side;
a first electrode disposed on the first side of the zirconia layer;
a second electrode disposed on the second side of the zirconia layer;
a channel structure on the first side of the zirconia layer in communication with ambient air and the first electrode, comprising a porous material configured to route air through the channel to the first electrode while preventing hydrocarbons from flowing through the channel and contacting the first electrode, such that a signal between the first and second electrodes is indicative of an amount of oxygen in exhaust gases contacting the second electrode.

2. The oxygen sensor of claim 1, wherein the porous material comprises porous alumina.

3. The oxygen sensor of claim 1, wherein the porous material comprises porous zeolite.

4. The oxygen sensor of claim 1, wherein a substantial portion of the channel structure has a uniform cross-sectional size.

5. The oxygen sensor of claim 1, wherein the first electrode is a reference electrode.

6. A method for manufacturing an oxygen sensor, comprising:
- disposing a first electrode on a first side of a zirconia layer;
- disposing a second electrode on a second side of the zirconia layer, the second side being opposite the first side;
- disposing a carbon-ceramic mixture on a first layer;
- disposing the first layer adjacent the zirconia layer such that the carbon-ceramic mixture is disposed adjacent the first electrode; and
- firing the zirconia layer, the first and second electrodes, the carbon-ceramic mixture, and the first layer to form the oxygen sensor such that the carbon-ceramic mixture transitions to a porous ceramic material that forms a channel structure in communication with ambient air and the first electrode, configured to route air through the channel to the first electrode while preventing hydrocarbons from flowing through the channel and contacting the first electrode.

7. The method of claim 6, wherein the carbon-ceramic mixture comprises carbon and alumina.

8. The method of claim 6, wherein the carbon-ceramic mixture comprises carbon and zeolite.

9. The method of claim 6, wherein a substantial portion of the channel structure has a uniform cross-sectional size.

10. The method of claim 6, wherein the first electrode is a reference electrode.

11. A system for determining an amount of oxygen in exhaust gases, comprising:
- an oxygen sensor having a zirconia layer, first and second electrodes and a channel structure, the zirconia layer having first and second sides, the second side being opposite the first side, the first electrode being disposed on the first side of the zirconia layer, the second electrode being disposed on the second side of the zirconia layer, the channel structure disposed on the first side of the zirzonia layer in communication with ambient air and the first electrode, and comprising a porous material configured to route air through the channel to the first electrode while preventing hydrocarbons from flowing through the channel and contacting the first electrode, such that a signal between the first and second electrodes is indicative of the amount of oxygen in exhaust gases contacting the second electrode; and
- a microprocessor configured to receive the signal from the oxygen sensor, the microprocessor further configured to determine an oxygen value corresponding to the amount of oxygen in the exhaust gases based on the signal, the microprocessor further configured to store the oxygen value in a memory device.

12. The system of claim 11, wherein the porous material comprises porous alumina.

13. The system of claim 11, wherein the porous material comprises porous zeolite.

14. The system of claim 11, wherein a substantial portion of the channel structure has a uniform cross-sectional size.

15. The system of claim 11, wherein the first electrode is a reference electrode.

* * * * *